(12) United States Patent
O'Connor et al.

(10) Patent No.: US 8,462,912 B2
(45) Date of Patent: Jun. 11, 2013

(54) COMPUTED TOMOGRAPHY EXAMINATION AND PARTICLE THERAPY TREATMENT

(75) Inventors: John P. O'Connor, Andover, MA (US); Charles Shaughnessy, Hamilton, MA (US)

(73) Assignee: Analogic Corporation, Peabody, MA (US)

(*) Notice: Subject to any disclaimer, the term of this patent is extended or adjusted under 35 U.S.C. 154(b) by 82 days.

(21) Appl. No.: 12/551,024

(22) Filed: Aug. 31, 2009

(65) Prior Publication Data

US 2011/0051891 A1    Mar. 3, 2011

(51) Int. Cl.
*A61N 5/10* (2006.01)
*G21K 5/08* (2006.01)

(52) U.S. Cl.
USPC ............................ 378/68; 378/65; 600/427

(58) Field of Classification Search
USPC ...................... 378/65, 68; 600/427
See application file for complete search history.

(56) References Cited

U.S. PATENT DOCUMENTS

| | | | |
|---|---|---|---|
| 2,781,454 A | 2/1957 | Green et al. | |
| 5,574,763 A * | 11/1996 | Dehner | 378/17 |
| 5,668,371 A * | 9/1997 | Deasy et al. | 850/1 |
| 6,307,914 B1 * | 10/2001 | Kunieda et al. | 378/65 |
| 6,385,288 B1 * | 5/2002 | Kanematsu | 378/65 |
| 6,560,310 B2 * | 5/2003 | Stark | 378/37 |
| 6,842,502 B2 | 1/2005 | Jaffray et al. | |
| 7,221,733 B1 * | 5/2007 | Takai et al. | 378/65 |
| 7,310,404 B2 * | 12/2007 | Tashiro et al. | 378/10 |
| 7,526,066 B2 | 4/2009 | Koshnitsky et al. | |
| 7,634,057 B2 * | 12/2009 | Ein-Gal | 378/69 |
| 7,640,607 B2 * | 1/2010 | Guertin et al. | 5/601 |
| 7,796,730 B2 * | 9/2010 | Marash et al. | 378/65 |
| 7,847,275 B2 * | 12/2010 | Lifshitz et al. | 250/505.1 |
| 7,953,205 B2 * | 5/2011 | Balakin | 378/69 |
| 2006/0285639 A1 | 12/2006 | Olivera et al. | |
| 2008/0317203 A1 * | 12/2008 | Ferrand et al. | 378/65 |

* cited by examiner

*Primary Examiner* — Thomas R Artman
(74) *Attorney, Agent, or Firm* — Cooper Legal Group LLC (57) ABSTRACT

An operation room may comprise both an object scanning apparatus for examining an object using x-ray radiation and an irradiation component for treating an object using particle radiation. A support article upon which the object may reside during (both) the examination and treatment may be configured to rotate about an axis substantially perpendicular to a plane through which x-ray radiation travels, may be configured to tilt with respect to the axis, and/or may be configured to yaw with respect to the axis. In this way, the relative orientation of the support article and the object remain substantially constant during the examination and treatment to facilitate treating a desired area of the object.

20 Claims, 4 Drawing Sheets

COMPUTED TOMOGRAPHY EXAMINATION AND PARTICLE THERAPY TREATMENT

BACKGROUND

The present application relates to the field of external beam radiotherapy. It finds particular application with particle therapy. It also relates to medical and other applications where an object is examined, or scanned, to determine a treatment plan and then treated according to the treatment plan using an external beam.

Cancer is one of the leading causes of death in humans. Advancements in medical technologies have played an intricate role in both identifying tumors in the early stages and treating the tumors by either slowing their growth or shrinking tumors to a size that can safely be removed or possibly extinguished. These advancements have also identified techniques and/or systems that are less invasive and less uncomfortable to a patient undergoing treatment than techniques and/or systems used in years past.

External beam radiotherapy, and in particular particle therapy, is a relatively recent development for the treatment of tumors. While it was suggested in the 1940s that particle technology could be capable of treating cancer, it was not implemented in a medical (e.g., hospital) setting until the 1990s. Since then, over sixty thousand patients, with over fifty different types of tumors, have been treated using particle therapy at the approximately thirty particle therapy treatment facilities all over the world.

External beam radiotherapy uses beams of protons, neutrons, ions, etc. to penetrate tissue and treat portions of a patient that have been identified as tumors. The beams are targeted at the tumor and are configured to damage the DNA of tissue cells of the tumor. Because tumors are generally not able to repair damaged DNA and/or repair damaged DNA more slowly than non-tumor cells, the beams may ultimately cause the cells to die (e.g., causing the tumor to shrink, possibly to the point of extinction).

Because the beams are configured to damage the DNA of tissue cells, it is important to mitigate the number of healthy cells that the beam contacts (e.g., particularly near the Bragg peak where the dose delivered to the tissue by the beam is at its maximum). Thus, generally before beams are emitted towards the tumor, a treatment plan is developed to identify a specific target region and/or to determine the characteristics of the particles that should be emitted toward the tumor, for example.

To generate a treatment plan, a patient is placed within a radiation scanner, such as a computed tomography (CT) scanner, and the patient is examined. During the examination, radiation is emitted from a radiation source towards the patient or, more particularly, towards a region of the patient in which the tumor is positioned (e.g., based upon diagnostic imaging). Radiation that traverses the patient is detected by a detector array positioned on a substantially diametrically opposite side of the patient relative to the radiation source. Using signals or data generated by the detector array (or, more generally, the radiation scanner) and indicative of the detected radiation, a treatment plan may be developed. Such a treatment plan may specify the precise orientation of the tumor in the patient, the desired trajectory of the beams (or rather, the orientation of an irradiation component emitting the beam relative to the patient), the types of particle to be used, and/or the energy at which particles should be accelerated (e.g., to yield a Bragg peak that falls within the tissue cells of the tumor), for example.

After the examination, the patient is moved from an examination room with the radiation scanner to a treatment room, where the particle radiation (also referred to as particle beams) may be delivered to the patient. Stated differently, the patient is positioned on a first support article (e.g., a first bed) for an examination, stands up and walks from an examination room to a treatment room, and is positioned on a second support article (e.g., a second bed) for treatment. Once positioned on the second support article, the patient may be treated as specified by the treatment plan (e.g., which was developed based upon an examination while the patient was positioned on the first support article).

Generally, the irradiation component is configured to emit particle beams in such a way as to cause the beams to impinge the tumor from a plurality of angles, or to impinge a plurality of locations on the tumor. For example, the irradiation component may be coupled to a rotating gantry that rotates about the patient (and the tumor) allowing the irradiation component to emit beams from a plurality of angles relative to the tumor. Stated differently, during treatment, the irradiation component may begin the treatment by emitting beams at a first orientation relative to the patient; the irradiation component may then be shut off (or a shutter may be positioned to block the beams from escaping the irradiation component), and the irradiation component may be rotated (by the rotating gantry) to a second orientation (different than the first orientation) relative to the patient. The irradiation component may then be turned back on (or the shutter removed), and a second set of beams may be emitted from the irradiation component. Such a technique may be referred to as "painting" the tumor (e.g., the beams impinge the tumor from a plurality of angles until a specified portion of tissue cells of the tumor have been struck by a beam).

While external beam radiotherapy and, more particularly, particle therapy have proven useful for treating numerous types of tumors, the adoption of particle therapy has been limited (to approximately thirty facilities) because of the cost of a particle therapy system, which may be on the order of hundreds of millions of dollars, and/or because of difficulties with getting the beam to hit the precise location specified in the treatment plan due to shifting of internal organs of the patient between the first support article (from which the treatment plan is developed) and the second support article (whereon treatment occurs).

SUMMARY

Aspects of the present application address the above matters, and others. According to one aspect, an apparatus is provided. The apparatus comprises an x-ray component configured to emit x-ray radiation onto an object. The apparatus also comprises an irradiation component configured to emit particle radiation onto the object.

According to another aspect, a method is provided. The method comprises emitting x-ray radiation onto an object that resides on a support article. The method also comprises emitting first particle radiation onto the object that resides on the support article while the object is positioned in a first position.

According to yet another aspect, an apparatus for particle therapy treatment is provided. The apparatus comprises a support article configured to support an object while the object undergoing an operation and a radiation source configured to emit x-ray radiation onto the object being operated upon during a first time interval. The apparatus also comprises a detector array configured to detect x-ray radiation that traversed the object being operated, wherein the detected x-ray radiation is used to develop a treatment plan. The apparatus further comprises an irradiation component configured to emit particle radiation onto the object being operated upon during a second time interval according to the treatment plan.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for creating a treatment plan and/or treating an object, or a patient, according to the treatment plan using external beam radiotherapy (e.g., particle therapy) are provided. That is, in one embodiment, one or more techniques and/or systems for examining an object to create a treatment plan and/or to treat the object with particle beams (e.g. proton, neutron, gamma, ion, etc.) or other beams (e.g., electron, photon, etc.) are provided.

Figure 1:
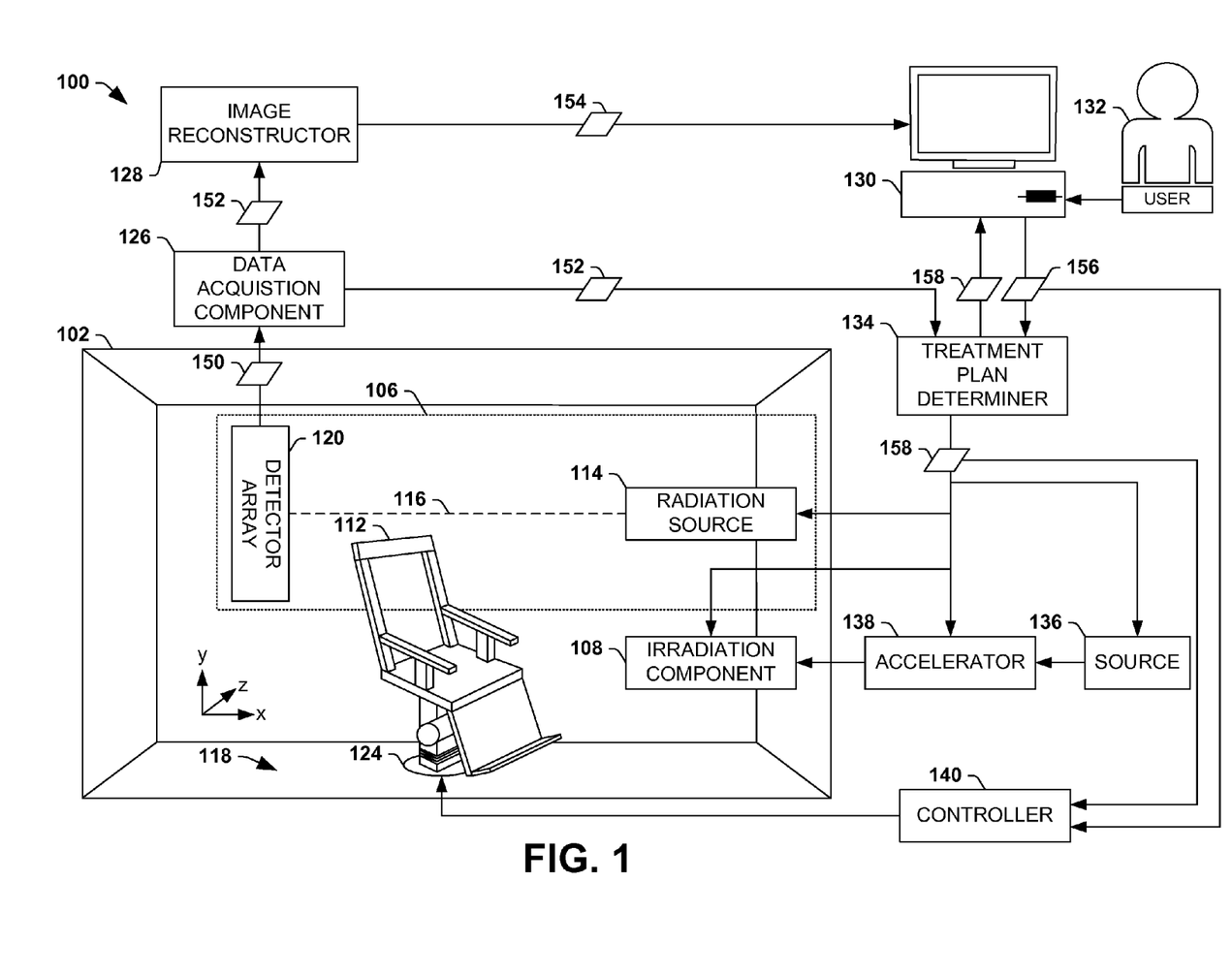
FIG. 1 is a schematic block diagram illustrating an example environment for examining an object and treating the object with particle radiation.

FIG. 1 is an illustration of an example environment 100 of an apparatus which may be employed for creating the treatment plan and/or treating an object (e.g., a human patient) (not illustrated). For example, the environment 100 may comprise a three-dimensional imaging scanner (e.g., a computed tomography (CT) scanner) for examining an object to create a treatment plan and/or a particle therapy system (e.g., an ion source, linear accelerator, synchrotron, irradiation component, etc.) for treating the object (e.g., to cause damage to and/or to remove a tumor from a patient).

The example environment 100 comprises an operation room 102 within which the object may be examined (to develop a treatment plan) and treated. The operation room 102 comprises an object scanning apparatus 106 (e.g., a CT scanner), an irradiation component 108, and a support article 112 (e.g. a chair, bed, etc.) configured to support the object. It will be appreciated that the room may have any suitable dimensions. Nevertheless, given that the scanning apparatus 106 and irradiation component 108 are both comprised within the room 102 and/or that the support article 112/patient is moved rather than the irradiation component 108 as described below, it will be appreciated that the room may be smaller than conventional rooms comprising a scanning apparatus or irradiation component. For example, the room may be 30 feet long by 30 feet wide by 12 feet tall.

The object scanning apparatus 106 comprises a radiation source 114 configured to emit x-ray radiation 116 (e.g., x-rays) in the form of a fan or cone beam towards the object upon which the operation is performed (e.g., the object under examination). As illustrated, the x-ray radiation 116 generally travels through one or more planes substantially parallel to a plane within a floor 118 of the operation room 102 lays. It will be appreciated that if the object scanning apparatus 106 comprised a rotating gantry (not shown) the rotating gantry would rotate about an axis substantially extending in the y-dimension (e.g., unlike the rotating gantry common in some CT scanners which rotates about an axis substantially extending in the z-dimension). Thus, the object scanning apparatus may be said to be a horizontally-based scanner.

The object scanning apparatus 106 also comprises a detector array 120 configured to detect x-ray radiation 116 that traversed the object. Generally, the detector array 120 is positioned on a substantially diametrically opposite side of the object relative to the radiation source 114. The detector array 120 is comprised of a plurality of pixels that detect x-ray radiation 116 and output signals and/or data 150 indicative of detected radiation, or indicative of the attenuation of the radiation as it traversed the object.

In the example environment 100, the support article 112 may be configured to rotate (e.g., 360 degrees) about an axis of rotation (e.g., extending in the y-dimension) on a rotational base 124 (e.g., powered by a motor (not shown)) relative to the floor 118 during an operation (e.g., examination) upon the object. In this way, three-dimensional data indicative of the object may be yielded from the detected radiation. That is, instead of rotating the radiation source 114 and/or the detector array 120 to acquire three-dimensional data (e.g., similar to what may occur in a tradition CT scanner), the support article 112 and the object may be rotated. It will be appreciated that such a configuration may save production, installation, and/or service cost because a rotating gantry (and a slip ring attached to the rotating gantry that may provide power and/or fluid to the rotating gantry) may not be present in the object scanning apparatus 106.

It will be appreciated that in another embodiment, the object scanning apparatus 106 comprises a rotating gantry (e.g., a donut-like structure) that is configured to rotate (e.g., through an x,z plane substantially parallel to the floor 118) about the object under examination. The radiation source 114 and/or the detector array 120 may be attached to the rotating gantry and configured to rotate about the object.

Thus, in some embodiments, the support article 112 may rotate, but the radiation source 114 and/or the detector array 120 may not rotate. In other embodiments the support article 112 may not rotate, but the radiation source 114 and/or the detector array 120 may rotate. In still other embodiments the support article 112, the radiation source 114, and the detector array 120 may all be configured to rotate about an axis substantially extending in the y-dimension.

It will be appreciated that the example environment 100 does not illustrate one or more gantries attaching the radiation source 114 and/or the detector array 120 to the operation room 102. Similarly, the example environment 100 does not illustrate a gantry coupling the radiation source 114 to the detector array 120. However, those skilled in the art will appreciate that some or all of such gantries may be part of the example environment 100.

In the example environment 100, a data acquisition component 126 is operably coupled to the object scanning apparatus 106 and is configured to receive the output signals, output data, and/or other information (collectively referred to herein as output data 150) from the detector array 120 or, more generally, the object scanning apparatus 106. Where the data acquisition component 126 receives output signals, the data acquisition component 126 may also be configured to filter the output signals using filtering techniques commonly known to those skilled in the art to improve the signal-to-noise ratio of the output signals.

The data acquisition component 126 may also be configured to compile the output data 150 that is received during a measuring interval (e.g., from the respective pixels) and generate projection space data 152. Such a compilation is at times referred to as a "view" or a "projection." A plurality of views may be generated from output data 150 that is generated during an examination of the object. Respective views may comprise output data 150 generated while the relative orientation between the object and the radiation source 114 changes. For example, a first view may comprise output data 150 generated while a patient was facing the radiation source 114 and a second view may comprise output data 150 generated while a patient was facing away from the radiation source 114. Of course, there can be many more views (e.g., between these two views), and these two views are merely intended to be non-limiting examples.

In the example environment 100, the projection space data 152 is transmitted to an image reconstructor 128 configured to receive the projection space data 152 (e.g., receive a plurality of views). The image reconstructor 128 is also configured to use analytical, iterative, or other reconstruction techniques known to those skilled in the art (e.g., 2D filtered back projection) to convert the projection space data 152 into one or more human perceptible images 154 of the object. Thus, the image reconstructor 128 converts that data from projection space to image space.

The example environment 100 also comprises a terminal 130 (e.g., a computer) configured to receive the one or more images 154. The image(s) 154 may be displayed on a monitor of the terminal 130 to a user 132 (e.g., medical personnel). In this way, the user 132 can inspect the image(s) 154 to verify that a tumor is within the portion of the object that is being examined, for example.

The terminal 130 may also be configured to receive user input from the user 132 which may provide instructions to a treatment plan determiner 134, a component of the object scanning apparatus 106, and/or the support article 112, for example. In this way, a user 132 may provide input into the examination and/or the treatment of the object, for example.

In the example environment 100, a treatment plan determiner 134 is configured to receive information 156 (e.g., user input, image(s) 154, etc.) from the terminal 130 and/or projection space data 152 from the data acquisition component 126. It will be appreciated that by receiving projection space data 152 (e.g. instead of and/or in conjunction with the image (s) 154), the treatment plan determiner 134 may use data that is free of image artifacts, caused by the image reconstruction process, and thus may more precisely identify a tumor, for example.

The treatment plan determiner 134 may be configured to use the information 156 and/or the projection space data 152 to generate a treatment plan 158 for the object undergoing the operation (e.g., the examination). The treatment plan 158 may, among others things, specify the precise position of the tumor in the patient, the trajectory that beams should travel (or rather, the orientation of an irradiation component emitting the beams relative to the object), the characteristics of the particles to be used (e.g., whether to use a carbon ion, proton ion, etc.), and/or the energy at which particles should be accelerated (e.g., to yield a Bragg peak that causes the beam to deliver a maximum dose within the tumor cells), for example. In this way, it can be determined how to target tumor cells without harming surrounding healthy tissue, for example. It will be appreciated that the treatment plan 158 may also comprise other information known to those skilled in the art and commonly included in a treatment plan for particle therapy techniques and/or systems.

As illustrated in the example environment 100, at least some portions of the treatment plan 158 may be transmitted to the terminal (e.g., so that the treatment plan 158 can be viewed by a user 132), a source 136 (e.g., so that particles with the correct characteristics can be selected), an accelerator 138 (e.g., so that the particles can be accelerated to the correct rate), an irradiation component 108 (e.g., so that the particle beams are emitted correctly), the radiation source 114 (e.g., so that the radiation source 114 can rescan the object between treatments), and/or a controller 140 (e.g., so that the controller 140 can instruct the rotational base 124 how to rotate), for example. It will be appreciated that the treatment plan 158 may also and/or instead be delivered to other components not discussed herein but are typically considered to be part of an examination and/or treatment system for external beam radiotherapy (e.g., a rotating gantry of a CT scanner). By way of example only and not limitation, a treatment plan may call for irradiating a tumor with different particles and/or with the same or different particles having different energies. This may be accomplished, for example, where the environment 100 comprises multiple irradiation components, accelerators, sources, etc. that could be operated independently to concurrently and/or consecutively treat at tumor with different particles and/or energies that may be directed at the tumor from different directions and/or angles. Moreover, as will be appreciated, since the relative orientation between the support article 112 and the patient can remain substantially fixed while the support article is moved, the tumor can continue to be precisely targeted when the support article/patient is moved to allow the tumor to be targeted by different particles and/or energies (e.g., because the patient's internal organs move little when the support article 112 is moved).

The example environment 100 also comprises a source 136 configured to generate and/or store the particles (e.g., protons, neutrons, ions, etc.), electrons, photons, etc. (herein collectively referred to as "particles") that are used to treat the object and/or other objects. Based upon information comprised within the treatment plan 158, the source 136 may emit particles with a particular characteristic. For example, the treatment plan 158 may specify that carbon ions be used to treat a tumor in a patient, and the source 136 may retrieve and/or emit the carbon ions as specified by the treatment plan 158.

In the example environment 100, an accelerator 138 is operably coupled to the source 136 and is configured to accelerate particles emitted from the source 136. It will be appreciated to those skilled in the art that the accelerator may be comprised of a linear accelerator, a circular accelerator (e.g., a synchrotron or cyclotron), and/or another particle accelerator known to those skilled in the art.

It will be understood to those skilled in the art that the acceleration rate may be dependent upon the size, shape, and/or orientation of the tumor within the object (e.g., a patient) and/or may be dependent upon the characteristics of the particles (e.g., proton, neutron, ion, electron, etc.) being used to treat the object. In this way, particle radiation, also referred to herein as particle beams, strike the tumor while the beams are delivering their maximum energy deposition (e.g., commonly referred to as their Bragg peak), for example. Thus, the accelerator 138 may also be operably coupled to the treatment plan determiner 134, and the treatment plan 158 may be used to determine the acceleration of the particles. For example, the treatment plan 158 may specify to use a proton particle and/or specify a particle acceleration rate, and the accelerator may be configured to accelerate the particle to the rate specified in the treatment plan 158.

The example environment further comprises the irradiation component 108 (e.g., an irradiation nozzle) 108 configured to emit particle radiation toward the object. It will be appreciated that the orientation (e.g., position) of the irradiation component 108 with respect to the operation room 102 may remain substantially constant while the object is being treated and/or the orientation of irradiation component 108 with respect to the operation room 102 may be altered while the object is being treated. For example, in one embodiment, the irradiation component 108 may be configured for vertical motion (e.g., moving up and/or down the page). That is, the irradiation component 108 may, but is not required to be, configured for movement (e.g., to facilitate "painting" a tumor).

The irradiation component 108 may comprise components and/or mechanisms commonly known to those skilled in the art. For example, the irradiation component 108 may comprise wire and/or ionization chambers (e.g., configured to monitor the particle radiation and/or to filter a portion of the particles from the particle radiation that is ultimately emitted from the irradiation component 108) and/or a shutter (e.g., configured to block the particle radiation from being emitted onto the object while the object is being repositioned). Similarly, the irradiation component 108 may comprise one or more scanning magnets configured to direct, or steer, the particle radiation towards the tumor (e.g., as specified in the treatment plan). In this way, mechanical limitations of the support article 112 (e.g., the ability of the support article 112 to position the object at a precise orientation relative to the irradiation component 108 within plus or minus 1 millimeters, for example) may be overcome by (slight) adjustments of the trajectory of the particle radiation, for example. By way of example only and not limitation, where the mechanical limitations of the support article 112 are on the order of a millimeter or so, but the irradiation component 108 and/or the radiation source 114 have sub-millimeter tolerances, such as 0.5 millimeter, for example, a particular area of interest can be more precisely targeted and/or examined by "tuning" the irradiation component 108 and/or radiation source 114 (and their accompanying components) instead of the support article 112.

In the example environment 100, a controller 140 is also operably coupled to the treatment plan determiner 134 and the terminal 130. The controller is configured to control the motion of the support article 112 based upon the treatment plan 158 and/or information 156 from the terminal 130. For example, the information 156 and/or the treatment plan 158 may specify an rpm for the support article 112 while the object is being examined by the object scanning apparatus 106. Similarly, the information 156 and/or treatment plan 158 may specify an orientation (e.g., height, rotational angle, yaw, tilt, etc.) of the support article 112 (and thus an orientation of the object) relative to the object scanning apparatus 106 and/ or the irradiation component 108, for example. And, such movement may be facilitated by the controller 140, for example.

Figure 2:
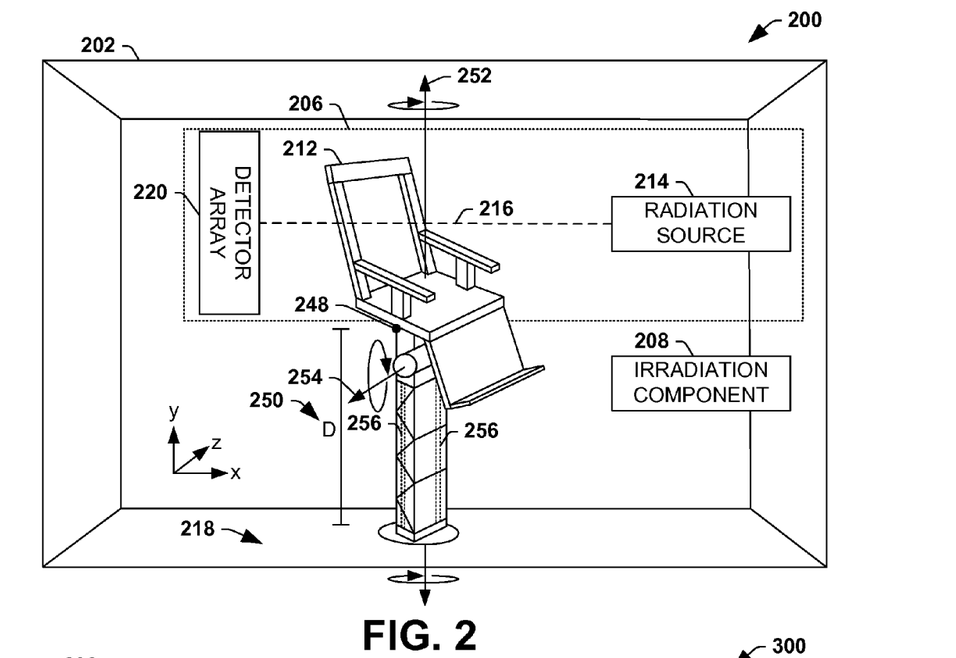
FIG. 2 illustrates an example operation room with a support article in a first orientation, the support article positioned in the first orientation when an object is being examined using x-ray radiation.
Figure 3:
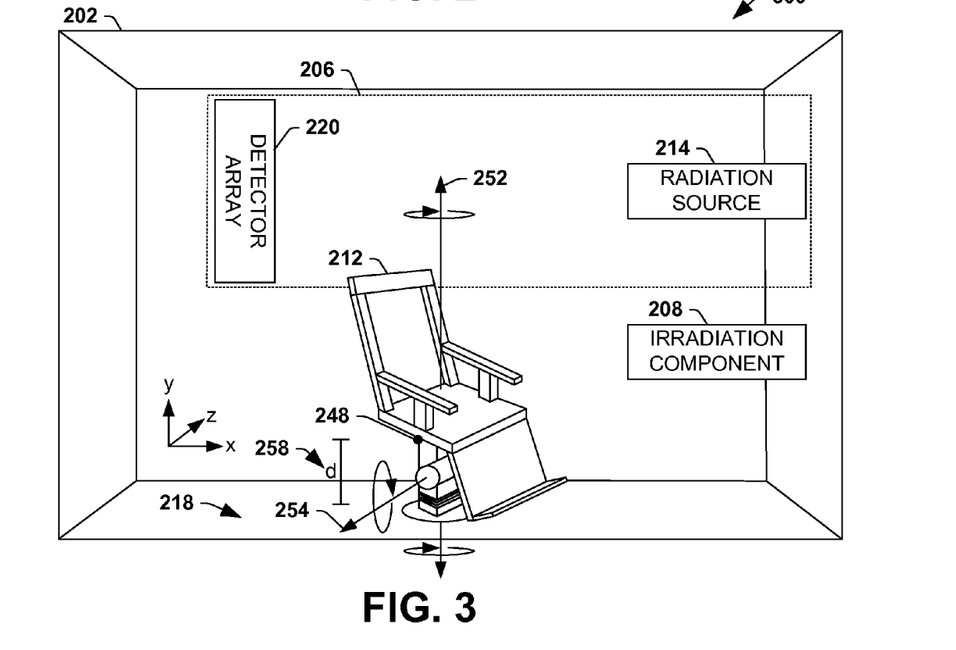
FIG. 3 illustrates an example operation room with a support article in a second orientation, the support article positioned in the second orientation when an object is being treated by particle radiation.

FIGS. 2-3 illustrate a first embodiment of an example operation room 202 (e.g., 102 in FIG. 1) that may be configured to both examine an object (not shown) using x-ray radiation and treat the object, or a portion thereof, using particle radiation. Stated differently, FIGS. 2-3 illustrate an operation room 202 within which an object scanning apparatus 206 (e.g., 106 in FIG. 1) and/or an irradiation component 208 (108 in FIG. 1) may be positioned.

FIG. 2 illustrates a support article 212 (e.g., 112 in FIG. 1) upon which the object resides is in a first orientation 200. While the support article 212 is in the first orientation 200, a first plane, parallel to a plane within which a floor 218 of the operation room 202 lays, passes through a predetermined point 248 on the support article 212. The distance between the two planes is represented by "D" 250.

While the support article 212 is in the first orientation 200 (and during a first time interval), the object scanning apparatus 206 may examine the object. That is, a radiation source 214 (e.g., 114 in FIG. 1) of the object scanning apparatus 206 may emit x-ray radiation 216 (e.g., 116 in FIG. 1) that is configured to traverse the object under examination, and a detector array 220 (positioned opposite the radiation source 214 with respect to the object) may detect such x-ray radiation (or attenuation thereof).

The support article 212 may be configured to rotate about a first axis 252 laying in a plane that is substantially perpendicular to a plane through which x-ray travels (e.g., and perpendicular to the first plane), recline or tilt relative to the first axis 252 about a second axis 254 laying in a plane that is substantially parallel to the plane through which x-ray radiation travels, and/or yaw (e.g., using two pistons 256 that may be adjusted independent of one another) before and/or during an examination of the object. For example, during the examination, the support article 212, and thus the object residing on the support article 212, may rotate about the first axis such that a three-dimensional scan of the object can be acquired. In this way, three-dimensional data (e.g., similar to data acquired from a conventional CT scanner) may be acquired without rotating the radiation source 214 and/or the detector array 220. It will be appreciated that in another embodiment, the radiation source 214 and/or detector array 220 may be coupled to a rotating gantry (not illustrated) that is configured to rotate through a plane (e.g., causing a circle to be formed within the plane) substantially parallel to the plane through which x-ray radiation travels.

It will be appreciated that a treatment plan determiner (e.g., 134 in FIG. 1) may develop a treatment plan (e.g., 158 in FIG. 1), used to treat the object, from the three-dimensional data that is acquired from the examination of the object by the object scanning apparatus 206. In this way, the object scanning apparatus 206 generates data that can be used in determining how, when, and from what positions to treat a portion of the object (e.g., a tumor in a patient).

FIG. 3 illustrates the support article 212 in a second orientation 300, different than the first orientation 200 illustrated in FIG. 2, with respect to the irradiation component 208. While the support article 212 is in the second orientation 300, a second plane, parallel to a plane within which the floor 218 of the operation room 202 lays, passes through the predetermined point 248 on the support article 212. The distance between the two planes is represented by "d" 258. Stated differently, as illustrated, the support article 212 was translated along the first axis 252 (e.g., the support article 212 was lowered) between the first orientation 200 depicted in FIG. 2 and the second orientation 300 depicted in FIG. 3.

While the support article 212 is positioned in the second orientation 300 (and at a second time interval), particle radiation may be emitted from the irradiation component 208 and directed towards a first location (e.g., specified in the treatment plan) of the object. In this way, a first set of particle beams may impinge a first predetermined portion of a tumor within the object, for example.

After a predetermined number of particles have impinged the first predetermined portion of the tumor, the irradiation component 208 may be shut off, or the beam may be shuttered, the support article 212 may be positioned in a third orientation, and a second set of particle beams may be directed at a second predetermined portion of the tumor. For example, the support article 212 (and the object) may be rotated about the first axis 252, rotated about the second axis 254, and/or yawed (e.g., using the two pistons 256) such that the particle beams impinge the tumor from a different perspective. In this way, a tumor, for example, may be painted by particles (e.g., causing tissue cells of the tumor to be struck by particles from a plurality of angles).

In one example, FIG. 2 and FIG. 3 may be said to illustrate an operation room 202 comprising an object scanning apparatus 206 configured to emit radiation substantially through at least a first plane and an irradiation component 208 configured to emit radiation through at least a second plane. The first and second planes can be substantially parallel to a plane upon which the floor 218 resides. The support article 212 is configured to position a patient (residing on the support article 212) in the first plane (at a first elevation) during an examination (to determine a treatment plan) and in the second plane (at a second elevation) during treatment (e.g., using particle radiation). In this way, the support article 212 may be configured to support the object both when x-ray radiation 216 is emitted from the radiation source 214 and when particle radiation is emitted from the irradiation component 208. Further, because the object can remain on the support article 212 during both the examination and the treatment, it may be said that the relative orientation of the support article 212 and the object remain substantially constant during both the examination and treatment. It will be appreciated that this may be advantageous as this may make it more likely that the internal organs of a patient remain relatively constantly positioned when the patient is both examined and treated. Thus, the treated area should more closely correspond to the area that is intended to be treated.

Similarly, given that there is often a time lag between detecting a tumor and treating a tumor, a tumor can initially be detected with x-ray radiation and a treatment plan developed. Then, prior to performing treatment with particle radiation, the location of the tumor can be quickly verified with x-ray radiation (typically at a lower dose of x-ray radiation than what was used to detect the tumor). This may be advantageous because a patient may move around considerably between diagnosis of and treatment of the tumor, and thus the tumor may shift around inside of the patient. Thus, verifying the location of the tumor just before treatment and maintaining the relative orientation between the patient and the support article 212 during both this verification and the treatment facilitates treating a desired area (e.g., the tumor).

Figure 4:
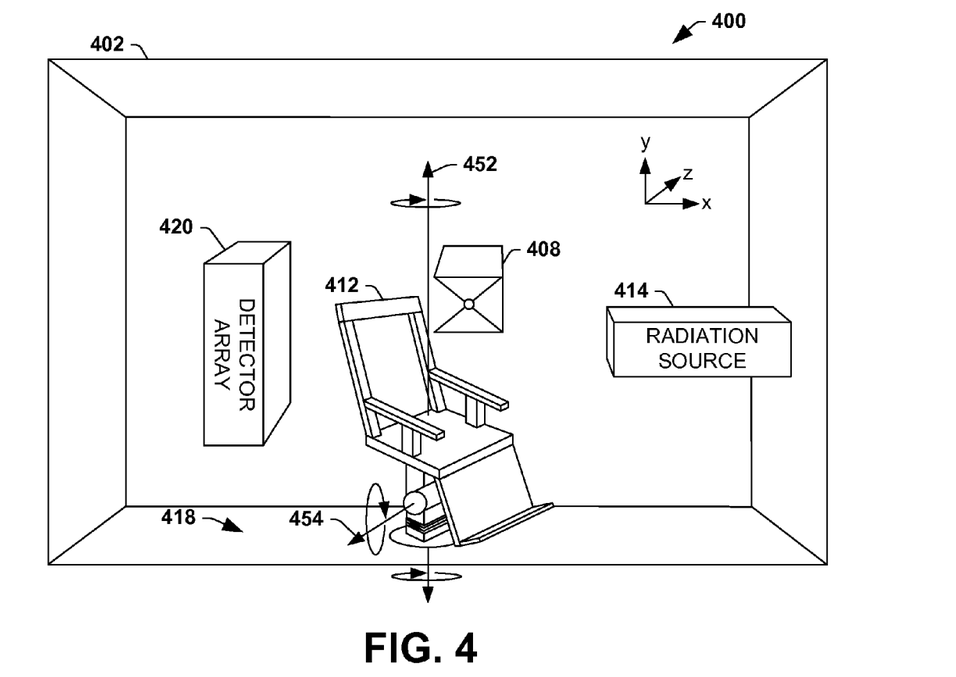
FIG. 4 illustrates an example operation room.

FIG. 4 illustrates a second embodiment of an example operation room 402 (e.g., 102 in FIG. 1) that may be configured to both examine an object (not shown) using (x-ray) radiation and treat the object using particle radiation. Stated differently, FIG. 4 illustrates an operation room 202 comprising an object scanning apparatus (e.g., 106 in FIG. 1) and an irradiation component 408 (108 in FIG. 1).

In such an embodiment, a radiation source 414 of the object scanning apparatus is configured to emit radiation in a first plane and the irradiation component 408 is configured to emit particle radiation in a second plane; the first and second planes being substantially coextensive. Thus, for example, the radiation source 414 and the irradiation component 408 can respectively emit x-ray radiation and particle radiation in substantially the same plane.

As illustrated, to allow both x-ray radiation and particle radiation to travel through the same plane (without interference), the radiation source 414, a detector array 420 of the object scanning apparatus (e.g., 120 in FIG. 1), and the irradiation component 408 can occupy different portions of the plane. For example, in the illustrated second embodiment 400, the irradiation component 408 is situated behind a support article 412 (e.g., 112 in FIG. 1) upon which the object resides and is configured to emit particle radiation that follows a path of a line coming out of the page. The radiation source 414 is situated to the right of the support article 412 and is configured to emit radiation that follows a path of a line traveling across (e.g., right to left) on the page. Similarly, the detector array 420 is situated to the left of the support article 412. In this way, the radiation source and/or the detector array 420 do not interfere with the particle radiation and vice-versa.

Like the support article in FIG. 1, the support article 412 can be configured to rotate about a first axis 452 substantially perpendicular to the plane through which x-ray radiation travels, to tilt or recline relative to the first axis 452 about a second axis 454 substantially parallel to the plane through which x-ray radiation travels, and/or to yaw relative to the first axis 452. The support article 412 can also, or instead, be configured for translation along the first axis (e.g., the support article 412 can be raised and lowered) such that the portion of the object that is to be examined and/or treated (e.g., a tumor) is at least partially positioned in the plane through which x-ray radiation and/or particle radiation travels, for example. In this way, the object scanning apparatus may perform a three-dimensional scan of the object and/or the irradiation component may emit particle radiation that impinges the object from a plurality of perspectives.

It will be appreciated that the example operation rooms 202 and 402 depicted in FIGS. 2-3 and 4 respectively are simply a few (of many) configurations in which an object scanning apparatus, an irradiation component, and a support article can be positioned in an operation room. Embodiments other than those herein described are also contemplated. For example, in another embodiment, an object scanning apparatus and/or irradiation component may be operably coupled to a lift, and the object scanning apparatus and/or the irradiation component may be raised and lowered while the support article remains at a substantially constant height with respect to the floor of the operation room during both the examination and the treatment. In yet another embodiment, the support article is shaped differently that the support article 212 and 412 depicted in FIGS. 2-3 and 4 respectively. For example, the support article may comprise a flat, bed-like surface upon which the object resides, and during an examination and/or treatment, the bed-like surface may be tilted 90 degrees such that a human patient, for example, would be in an upright, standing position. In this way, a human patient may be treated more easily for tumors that would be difficult to view, or access (e.g., with x-ray and/or particle radiation), if the human patient was sitting down, for example. Additionally, the support article may comprise and/or have one or more straps and/or other like mechanisms associated therewith so that a patient may be steadied during examination and/or treatment (e.g., so that a desired area is treated).

Figure 5:
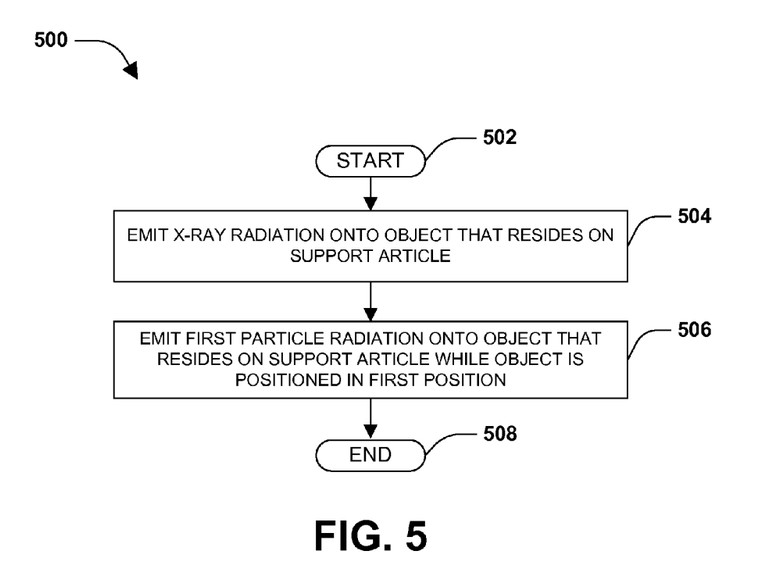
FIG. 5 is a flow diagram illustrating an example method for examining an object using x-ray radiation and treating the object using particle radiation.

FIG. 5 illustrates an example method 500. Such a method 500 may be used to examine an object and/or treat an object based upon a treatment plan developed from the examination. For example, such a method 500 may be used to acquire three-dimensional data indicative of the object and/or to treat a portion of the object based upon a treatment plan yielded from the three-dimensional data without changing the orientation of the object with respect to a support article upon which the object resides between the examination and the treatment.

The example method 500 begins at 502 and x-ray radiation is emitted onto the object that resides on the support article at 504. Generally, the x-ray radiation is emitted in the form of a fan or cone beam (e.g., a beam comprised of a plurality of fans), and at least one fan travels through a first plane that is substantially parallel to a floor of an operation room in which the operation (e.g., an examination) is performed.

As the radiation travels through the first plane, the support article may be configured to rotate about an axis that lays in a second plane substantially perpendicular to the first plane. In this way a three-dimensional scan of the object may be performed and three-dimensional data may be generated (e.g., to acquire data similar to data produced in a convention CT scanner). Because the support article, and therefore the object residing on the support article, is rotated, the radiation source (and/or a detector array configured to detect radiation) may not rotate. That is, the radiation source can be on a rotating gantry that is configured to rotate in the first plane, but the radiation source is not required to rotate to acquire three-dimensional data. Thus, a rotating gantry or other mechanism for rotating the radiation source (and/or detector array) is optional.

Radiation that traverses the object upon which the operation (e.g., examination) is performed is detected by a detector array (e.g., a multi-channel detector comprised of a plurality of elements, respective elements comprised of a plurality of pixels). The detector array is configured to emit output signals and/or output data indicative of the object upon which the operation is performed, or indicative of the radiation that traversed the object. Using such output signals and/or output data, a treatment plan that may be used for treating the object (e.g., using particle radiation) may be generated. For example, a treatment plan may specify characteristics of particle radiation (e.g., type of particle, acceleration rate, etc.) emitted toward the object.

The support article can be configured to reorient the object before x-ray radiation is emitted, while x-ray radiation is emitted, after x-ray radiation is emitted, and/or in between emissions of particle radiation, for example. In one example, as previously discussed, the support article may be configured to rotate relative to an axis lying in a plane substantially perpendicular to a plane through which a fan beam of x-ray radiation travels. In another example, the support article is configured to tilt or recline (e.g., moved back and/or forth) with respect to the axis. In yet another example, the support article may be configured to yaw (e.g., moved side-to-side) with respect to the axis. In another example, the support article may be configured to be translated along the axis (e.g., altering the distance between the floor of the operation room and the object). In this way, the orientation of the object with respect to the radiation source and/or an irradiation component that is configured to emit particle radiation may be altered without substantially altering the relative orientation of the object and the support article.

At 506, first particle radiation is emitted onto the object that resides on the support article while the object is positioned in a first position. It will be appreciated that "particle radiation" is used broadly herein to refer to proton, neutron, ion, electron, proton and/or other beam commonly used in external beam radiotherapy and known to those skilled in the art. Generally, the relative orientation between the support article and the object is maintained, or remains substantially constant, when both the x-ray radiation and the first particle radiation are emitted. That is, the object is placed in a first orientation with respect to the support article while the x-ray radiation is emitted and maintains the first orientation while the first particle radiation is emitted.

For example, to maintain the relative orientation of the object and the support article during both the emission of x-ray radiation and the emission of particle radiation, the object can be secured, or strapped, to the support article before x-ray radiation is emitted. The x-ray radiation can then be emitted, a treatment plan can be developed, and the particle radiation can be emitted while the object remains secured to the support article. Once the (first) particle radiation is emitted and/or the operation (e.g., examination and treatment) is completed, for example, the object may be unsecured from the support article. In this way, the position of the object relative to the support article remains substantially constant during both the examination to develop the treatment plan and the actual treatment, for example.

It will be appreciated to those skilled in the art that there are numerous configurations that would promote both the examination (using x-ray radiation) and treatment (using particle radiation) while maintaining the relative orientation of the object and the support article. For example, in one embodiment, the orientation of the object with respect to an irradiation component that is configured to emit the particle radiation changes between a first time interval when the x-ray radiation is emitted and a second time interval when the first particle radiation is emitted. That is, the object may have a first orientation with respect to the irradiation component when x-ray radiation is emitted and a second orientation with respect to the irradiation component when the first particle radiation is emitted. In one example, the first orientation causes the object to reside in a first plane and the second orientation causes the object to reside in a second plane that is different than the first plane, the first plane and second plane substantially parallel to a third plane through which x-ray radiation travels (e.g., the support article is lowered before the first particle radiation is emitted). In another example, the first and second planes are co-extensive, but the irradiation component and the radiation source are at different rotational angles with respect to the support article (e.g., as illustrated in FIG. 4).

In one embodiment, after the first particle radiation has been emitted, the object is rotated about the axis from the first position to a second position and/or the object (and the support article) is titled or yawed with respect to the axis. Once repositioned to a second position, second particle radiation can be emitted onto the object residing on the support article. In this way, a second portion of the object can be exposed to particle radiation. Stated differently, in this way, a tumor, for example, can be exposed to particle radiation from a plurality of angles (e.g., painting a large portion of tissue cells comprised within the tumor).

It will be appreciated that the acts of emitting x-ray radiation and/or emitting particle radiation may be repeated a plurality of times and from a plurality of angles. In this way, a plurality of treatment plans can be developed and/or an object may be treated by a plurality of particle beams. For example, a patient can be examined, a first treatment plan can be developed, a tumor within the patient can receive a first set of particle beams from a plurality of angles, the patient can be reexamined (to determine how the particle beams are affecting the tumor), and the tumor can receive a second set of particle beams from a plurality of angles. Such acts may be accomplished without changing the relative orientation of the object and the support article, for example.

In another example, since there may be a time lag between detecting a tumor and treating a tumor, a tumor can initially be detected with x-ray radiation and a treatment plan developed. Then, prior to performing treatment with particle radiation, the location of the tumor can be quickly verified with x-ray radiation (typically at a lower dose of x-ray radiation than what was used to detect the tumor). This may be advantageous because a patient may move around considerably between diagnosis of and treatment of the tumor, and thus the tumor may shift around inside of the patient. Thus, verifying the location of the tumor just before treatment and maintaining the relative orientation between the patient and the support article 212 during both this verification and the treatment facilitates treating a desired area (e.g., the tumor).

The example method 500 ends at 508.

Figure 6:
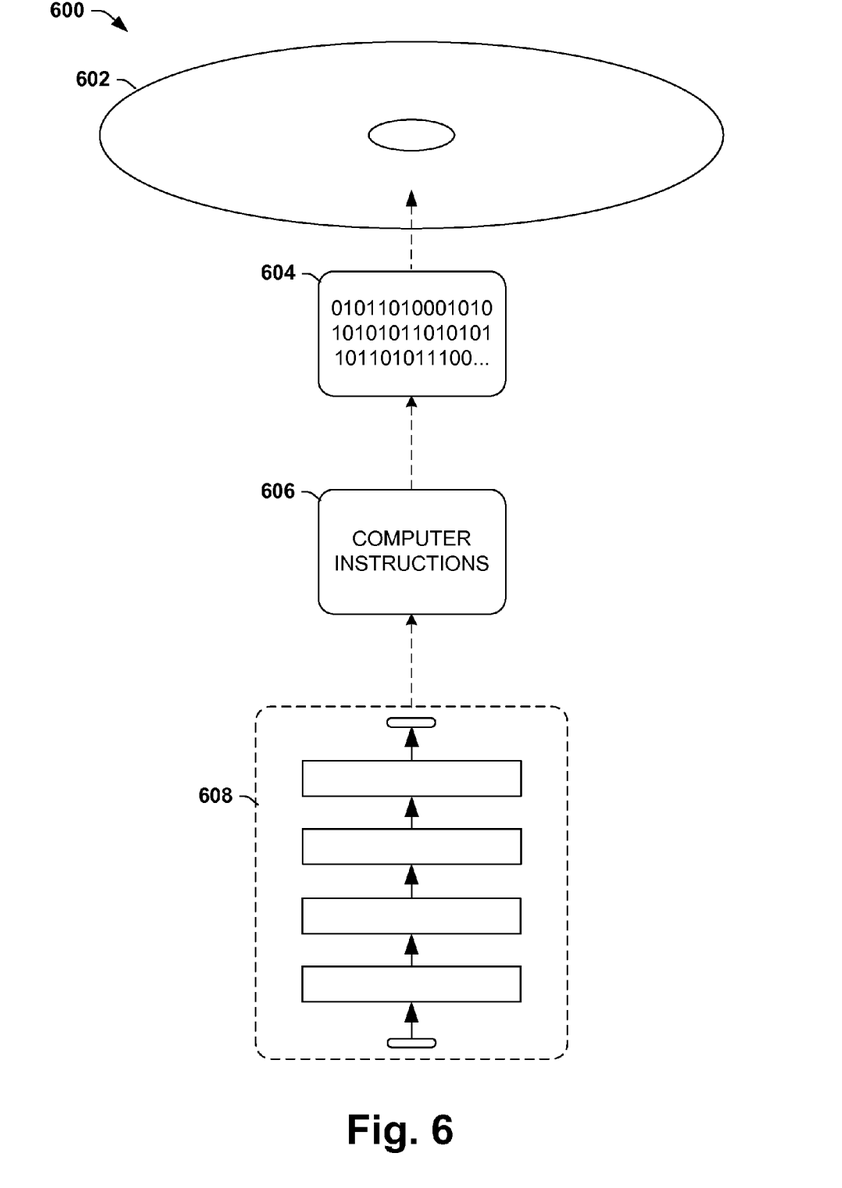
FIG. 6 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 6, wherein the implementation 600 comprises a computer-readable medium 602 (e.g., a CD-R, DVD-R, or a platter of a hard disk drive), on which is encoded computer-readable data 604. This computer-readable data 604 in turn comprises a set of computer instructions 606 configured to operate according to one or more of the principles set forth herein. In one such embodiment 600, the processor-executable instructions 606 may be configured to perform a method 608, such as the example method 500 of FIG. 5, for example. In another such embodiment, the processor-executable instructions 606 may be configured to implement a system, such as at least some of the exemplary environment 100 of FIG. 1, for example. Many such computer-readable media may be devised by those of ordinary skill in the art that are configured to operate in accordance with one or more of the techniques presented herein.

It will be appreciated that there are numerous benefits to the techniques and/or systems described herein. For example, neither the object scanning apparatus (e.g., 106 in FIG. 1) nor the irradiation component may (necessarily) comprise a rotating gantry, thus reducing the cost over conventional systems. Similarly, the relative orientation of the object and support article may be substantially constant during both the examination and the treatment. Thus, organs may be in the same relative orientation during treatment as they were during the examination (e.g., promoting precision of the particle beams on the intend target). Further, the object scanning apparatus may be oriented in such a way that components comprised within the object scanning apparatus do not interfere with the particle radiation and vice-versa.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An apparatus for particle therapy, comprising:
a support article configured to support an object while the object is undergoing an examination and a treatment;
an examination apparatus for examining the object, comprising:
an X-ray source configured to emit X-ray radiation onto the object, the X-ray radiation traversing a first plane substantially parallel to a plane of a floor of an examination room within which at least a portion of the apparatus for particle therapy resides, and
a detector array configured to detect X-ray radiation that traversed the object; and
a treatment apparatus for treating the object, comprising:
an irradiation component configured to emit particle radiation onto the object, the particle radiation traversing a second plane substantially parallel to the plane of the floor,
the examination apparatus and the treatment apparatus substantially fixed in the examination room during the examination and the treatment,
the support article configured to rotate the object relative to the examination apparatus and the treatment apparatus, and
the examination apparatus configured to not occlude the treatment apparatus relative to the object during the examination of the object.

2. The apparatus of claim 1, comprising a treatment plan determiner configured to develop a treatment plan based at least in part upon the examination, and the treatment apparatus configured to treat the object according to the treatment plan.

3. The apparatus of claim 1, the support article configured for vertical motion.

4. The apparatus of claim 3, the support article configure to position the object at a first vertical height relative to the floor during the examination and to position the object at a second vertical height relative to the floor during the treatment.

5. The apparatus of claim 1, the support article configured to rotate the object during the examination to facilitate acquisition of volumetric data representative of the object.

6. The apparatus of claim 1, a relative orientation of the examination apparatus and the treatment apparatus remaining substantially constant during both the examination and the treatment.

7. The apparatus of claim 1, the support article configured to tilt relative to an axis of rotation about which the support article is configured to rotate.

8. The apparatus of claim 1, wherein the first plane and the second plane are co-planar.

9. The apparatus of claim 1, a relative orientation between the support article and the object remaining substantially constant during both the examination and the treatment.

10. The apparatus of claim 1, the X-ray source and the detector array substantially fixed in the examination room such that the object is examined without rotating the X-ray source and without rotating the detector array relative to the object.

11. A particle therapy treatment method, comprising:
  examining an object, the examination comprising:
    emitting X-ray radiation from an X-ray source onto the object while the object is in a first orientation relative to the X-ray source, the X-ray radiation traversing a first plane substantially parallel to a plane of a floor of an examination room,
    rotating the object relative to the X-ray source such that the object is in a second orientation relative to the X-ray source, and
    emitting second X-ray radiation from the X-ray source onto the object while the object is in the second orientation relative to the X-ray source, the second X-ray radiation traversing the first plane; and
  treating the object, the treatment comprising:
    emitting particle radiation from an irradiation component onto the object, the particle radiation traversing a second plane substantially parallel to the plane of the floor, the irradiation component and X-ray source substantially fixed in the examination room wherein the object is examined and treated, and
    supporting the object on a same support article during the examination and the treatment, where the support article rotates the object from the first orientation to the second orientation.

12. The method of claim 11, comprising determining a treatment plan for the object based at least in part upon the examination of the object, and wherein treating the object comprises treating the object according to the treatment plan.

13. The method of claim 11, examining the object comprising examining the object without occluding, by the X-ray source, the irradiation component relative to the object.

14. The method of claim 11, comprising maintaining a relative orientation between the object and the support article during the examination and the treatment of the object.

15. The method of claim 11, comprising adjusting a distance between the object and the floor of the examination room between the examination of the object and the treatment of the object.

16. The method of claim 11, wherein the first plane and the second plane are co-planar.

17. The method of claim 11, examining the object comprising examining the object to generate volumetric data representative of the object.

18. The method of claim 11, comprising tilting the support article, relative to an axis of rotation about which the support article rotates, during the treatment of the object.

19. An apparatus for particle therapy, comprising:
  a support article configured to support an object while the object is undergoing an examination and a treatment;
  an examination apparatus for examining the object, comprising:
    an X-ray source configured to emit X-ray radiation onto the object, the X-ray radiation traversing a first plane substantially parallel to a plane of a floor of an examination room within which at least a portion of the apparatus for particle therapy resides, and
    a detector array configured to detect X-ray radiation that traversed the object;
  a treatment plan determiner configured to develop a treatment plan for the object based at least in part upon the examination of the object; and
  a treatment apparatus for treating the object according to the treatment plan, the treatment apparatus comprising:
    an irradiation component configured to emit particle radiation onto the object, the particle radiation traversing a second plane substantially parallel to the plane of the floor,
  the examination apparatus and the treatment apparatus substantially fixed in the examination room during the examination and the treatment such that a relative orientation of the examination apparatus and the treatment apparatus remains substantially constant during both the examination and the treatment, and the support article configured to rotate the object relative to the examination apparatus and the treatment apparatus.

20. The apparatus of claim 19, the examination apparatus configured to not occlude the treatment apparatus relative to the object during the examination of the object.

* * * * *